Figure 1:
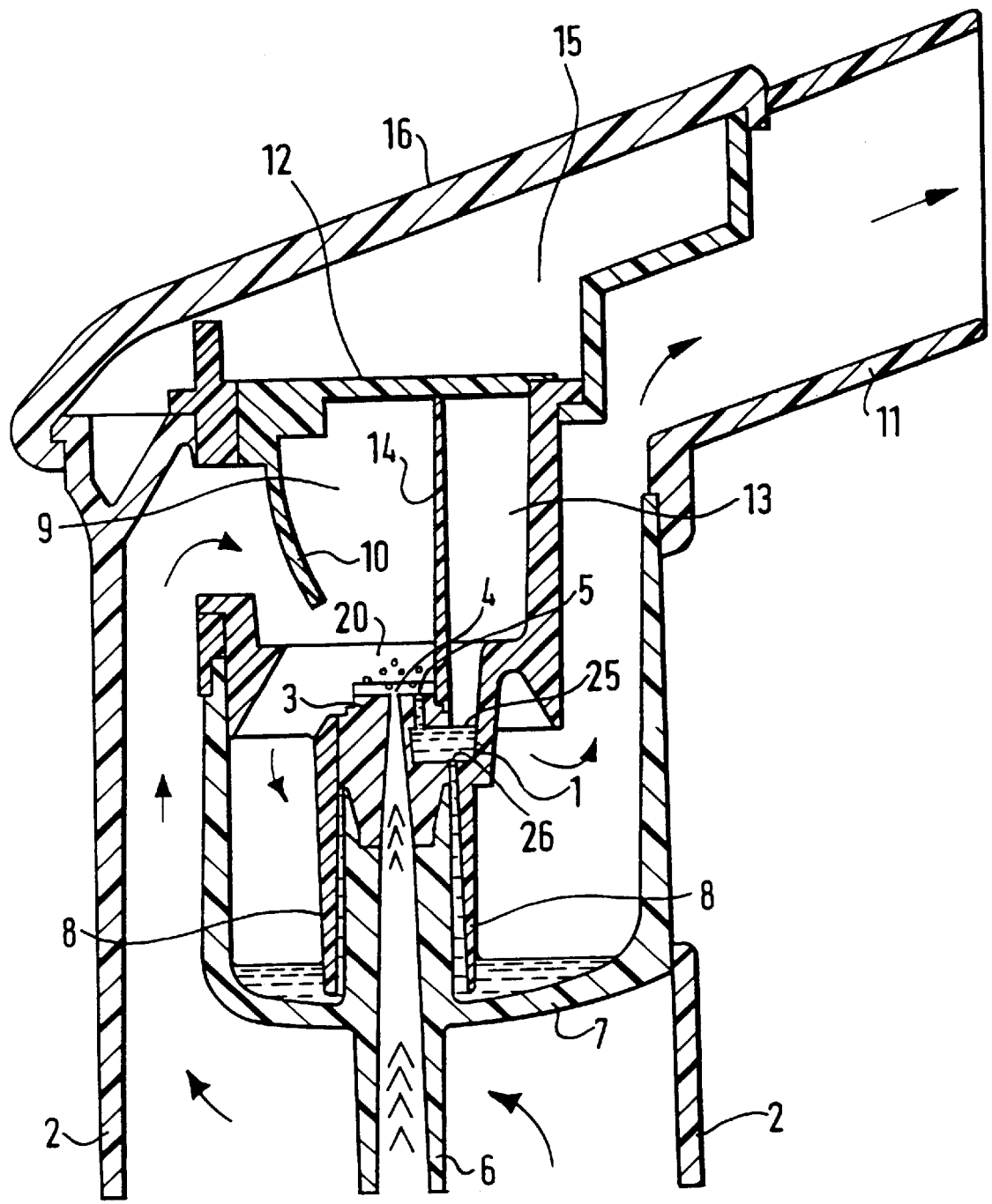

United States Patent
Pitcher et al.

[11] Patent Number: 6,129,080
[45] Date of Patent: Oct. 10, 2000

[54] ATOMIZER

[75] Inventors: Jay Pitcher, Epping; David Le Cheminant, Newtown, both of Australia; Jonathan Stanley Harold Denyer, Pagham, United Kingdom

[73] Assignee: Medic-Aid Limited, United Kingdom

[21] Appl. No.: 09/013,727

[22] Filed: Jan. 27, 1998

[30] Foreign Application Priority Data

Jan. 27, 1997 [GB] United Kingdom .................. 9701621

[51] Int. Cl.⁷ .................................................. A61M 11/00
[52] U.S. Cl. .............................. 128/200.21; 128/200.14; 128/200.18
[58] Field of Search ................ 128/200.21, 200.18, 128/200.14, 200.23, 203.25, 205.11, 204.25, 204.26, 204.23

[56] References Cited

U.S. PATENT DOCUMENTS

| 2,535,844 | 12/1950 | Emerson | 123/195 |
| 3,603,308 | 9/1971 | Spradling et al. | 128/145.8 |
| 4,396,015 | 8/1983 | Johnson | 128/200.14 |
| 5,080,093 | 1/1992 | Raabe et al. | 128/200.21 |
| 5,099,833 | 3/1992 | Michaels | 128/200.16 |
| 5,312,046 | 5/1994 | Knoch et al. | 239/338 |
| 5,533,501 | 7/1996 | Denyer | 128/200.21 |
| 5,549,102 | 8/1996 | Lintl et al. | 128/200.21 |
| 5,570,682 | 11/1996 | Johnson | 128/200.14 |
| 5,687,912 | 11/1997 | Denyer | 239/343 |
| 5,823,179 | 10/1998 | Grychowski et al. | 128/200.18 |

FOREIGN PATENT DOCUMENTS

| 627266 A2 | 12/1994 | European Pat. Off. . |
| 2751883 | 8/1986 | France . |
| 1138274 | 12/1994 | United Kingdom . |
| WO89/06147 | 7/1989 | WIPO . |

*Primary Examiner*—John G. Weiss
*Assistant Examiner*—Todd M. Martin
*Attorney, Agent, or Firm*—William A. Simons; Wiggin & Dana

[57] ABSTRACT

An atomizer for dispensing a powder or liquid product which is atomized by a stream of compressed air and further has either (1) means to prevent or stop the product from atomizing in response to a positive pressure in the atomizer or (2) a secondary reservoir located between the product reservoir and a product outlet from which the product is atomized, said secondary reservoir is in fluid connection with a second chamber, the second chamber being operable in response to a positive pressure in the atomizer to drive fluid from the secondary reservoir.

17 Claims, 3 Drawing Sheets

ATOMIZER

BACKGROUND OF THE INVENTION

1. Field of the Invention

This invention relates to atomizers, in particular, atomizers for dispensing powders or liquids which are atomized by a stream of compressed air. Such atomizers may, for example, be used as medical atomizers or dispensing small quantities of medicaments.

2. Brief Description of Art

Most conventional atomizers of the above type operate continuously whether atomization is required or not. Strictly speaking, when such atomizers, frequently called nebulizers, are used in medical applications, atomization is only required during the inhalation phase of a breathing cycle so that a drug can be administered by deposition in the lungs. In practice a patient usually inhales for about 30 percent of the breathing cycle, consequently, use of a continuously operating atomizer results in a large proportion of the atomised drug being wasted.

Some designs of medical atomizer overcome such wastage by giving the patient a manual trigger to start the atomization when they begin to inhale. Such a manual trigger controlled type of atomizer is not satisfactory since the patient must coordinate inhalation with trigger operation.

Figure 2:
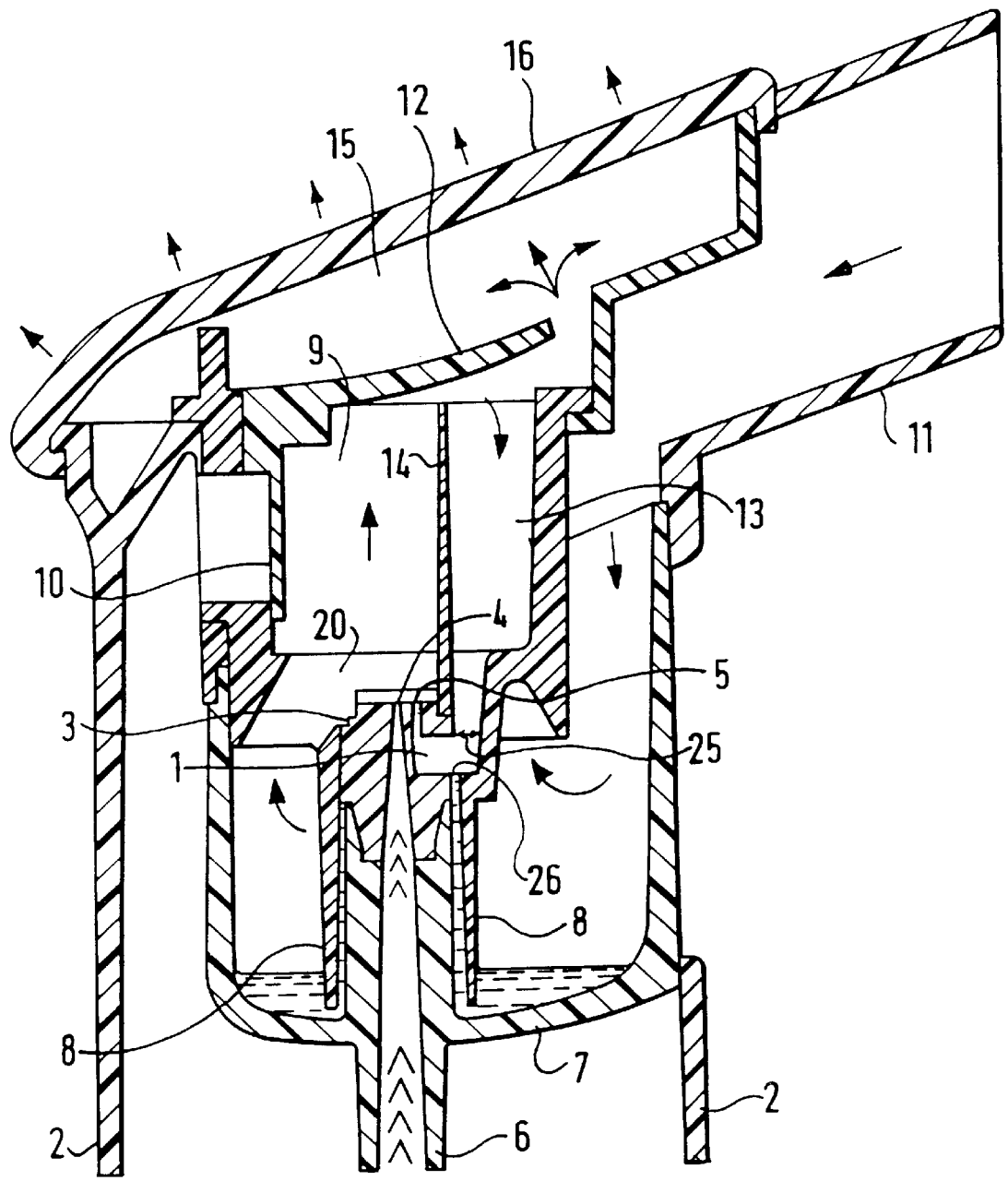
Figure 3:
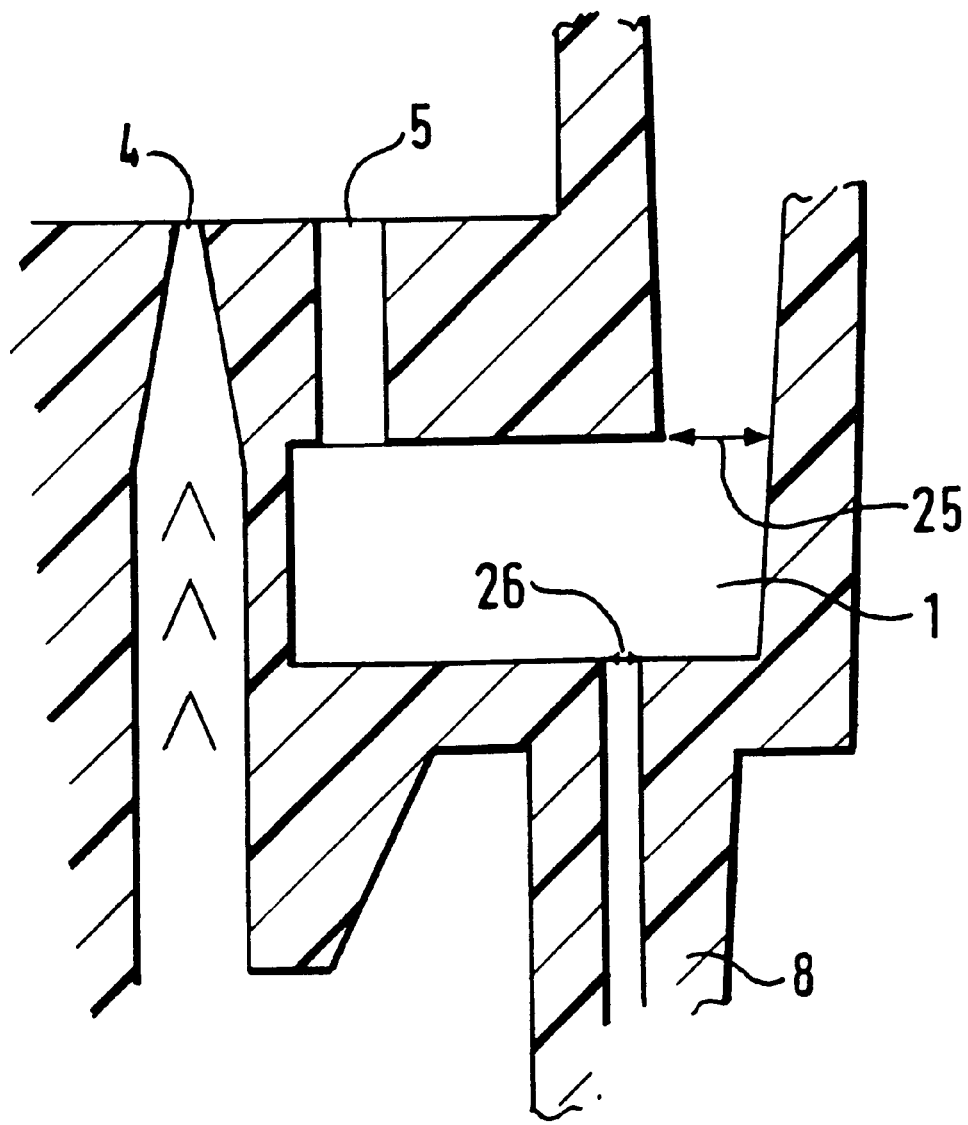

In one conventional atomizer a gas duct leads qas under pressure to a gas exit, a reservoir for holding the substance to be atomised is formed around the base of the gas duct, and a sleeve placed around the gas duct defines a passageway through which the substance to be atomised may pass to at least one outlet. A fixed deflector in the form of a bar is disposed in line with the gas outlet so that gas issuing from the gas exit is deflected so as to pass over the outlet or outlets. The passage of gas over each outlet draws the substance to each outlet. The deflected gas atomizes the substance, and atomized particles of the substance are carried away by the stream of deflected gas, and are subsequently inhaled during the inhalation phase of the patient. Since the patient breathes air or gas in through the atomizer, but only inhales through part of the cycle, some of the drug is lost while the patient is not inhaling.

An example of such an atomiser system is to be found in EP-A-627,266 (Medic-Aid Limited).

BRIEF SUMMARY OF THE INVENTION

In a first aspect of the invention there is provided an atomizer comprising an atomizer jet, the atomizer jet having a product outlet from which product can be atomized, means for sourcing compressed air, a product reservoir, means for supplying the product from the reservoir to the outlet and a first chamber into which atomized product can diffuse, characterized in that the atomizer has means to prevent or stop the product from atomizing in response to a positive pressure in the atomizer.

According to a further aspect of the invention, there is provided an atomizer comprising an atomizer jet, the atomizer jet having a product outlet from which product can be atomized, means for sourcing compressed air, a product reservoir, a means supplying the product from the reservoir to the outlet and a first chamber into which atomized product can diffuse, characterized in that the atomizer has located between the product outlet and the reservoir a secondary reservoir which is in fluid connection with a second chamber, the second chamber being operable in response to a positive pressure in the atomizer to drive fluid from the secondary reservoir.

DETAILED DESCRIPTION OF THE INVENTION

In embodiments of the invention, it is preferred that the apparatus is one which generates atomized product when the pressure in the apparatus is atmospheric or less than atmospheric (i.e. negative), but that atomisation is prevented or stopped when the pressure in the apparatus is positive (i.e. greater than atmospheric).

In embodiments of the invention, the nebulizer may dose the medicament to the user via a mouthpiece, though it is envisaged that atomized medicament could be dosed to the user through a sealing face mask.

The invention is further described by way of example only, with reference to the accompanying drawings, in which:

FIG. 1 shows a schematic cross-section of an embodiment of the invention in use with the user inhaling;

FIG. 2 shows a schematic cross-section of the embodiment of FIG. 1 in use with the user exhaling; and FIG. 3 shows an enlarged schematic cross section view of a secondary reservoir 1 in the embodiment of FIG. 1.

Referring to the figures, the atomizer includes a gas duct 6 which provides gas under pressure (show as a series of arrowheads in gas duct 6) from a compressed air source to a gas exit 4 within a jet head 3. The gas duct 6 passes through a wall of a reservoir 7 within which a substance to be atomized such as a medicament is held. A sleeve 8 is disposed around the jet head 3 and the gas duct 6. Passages are formed between the inner surface of the sleeve 8 and the outer surface of the gas duct 6 for leading the substance to be atomized from the reservoir 7 to a secondary reservoir 1, which has an exit to outlet 5 in the jet head adjacent to the gas exit 4.

For atomization of the substance to take place, gas exiting from the gas exit 4 passes close to the outlet 5. In a manner well known in the art, gas exiting from gas exit 4 flows at high speed into baffle bar 20, which is located generally at the bottom of a first chamber 9, and it is this collision of gas which generates the appropriate conditions in which to cause atomisation of medicament. The atomization of medicament at outlet 5 causes substance to be atomised to be drawn from the reservoir 7, through the passage between the sleeve 8 and the gas duct 6, and up through secondary reservoir 1 to the outlet 5. The flow of pressurized air when it has rebounded off of baffle 20 atomizes the substance as the substance leaves the outlet 5.

Further information on the atomisation procedure may be found in U.S. Pat. No. 5,533,501

It is important that the substance is atomized into very fine droplets. In medical applications, the substance to be atomised is a drug for administering to a patient by lung deposition. The finer the droplets, the deeper into the lungs the drug will pass. This maximises the deposition of the drug.

The atomizer also has a housing portion 2 which vents to be outside by which atmospheric air may enter the atomizer. However, mounted on top of gas duct 6, and integral therewith is first chamber 9 which opens towards housing portion 2, but is separated therefrom by a first one way valve 10. First one way valve 10 is resiliently deformable, and configured so as to only open and allow air from housing portion 2 into the atomizer when the user is inhaling, and hence when a reduced or negative pressure is created in first chamber 9. This is the configuration of the device shown in FIG. 1.

The atomizer is provided with a mouthpiece 11, which is in communication with a head space above reservoir 7, and with the first chamber 9, through which the user inhales and exhales. First chamber 9 has also located at its end remote from the gas exit 4 a second one way valve 12, which is configured to open only when the user is exhaling, and hence there is a positive pressure in first chamber 9, as shown in FIG. 2.

First chamber 9 is separated from a second chamber 13 by a rigid sidewall 14, with sidewall 14 in one direction extending down towards and connecting with jet head 3, and in the other direction being also closed by second one way valve 12. Second chamber 13 is generally circular in cross section and bounded by sidewall 14, and is configured such that it also has an exit into secondary reservoir 1. Second one way valve 12 is made of a resilient material, and is configured so as to close both first chamber 9 and second chamber 13 simultaneously when there are no positive or reduced pressures in the atomizer.

In order that the atomizer is configured so as to function smoothly, it has been found preferable that the area of second one way valve 12 covering the first chamber 9 is substantially greater than the area of the second one way valve 12 covering the second chamber 13, and preferably is greater by a ratio of at least 10:1. If this is not the case, in the exhalation phase of use the pressure on the second one way valve may be too high to allow it to open properly.

Located on the side of the second one way valve 12 is a space 15, which is bounded by a resilient filter 16. Filter 16 is air permeable, though it could also be airtight in various embodiments.

It has also been found desirable in constructing the atomizer according to the invention that the entrance to the second reservoir 1 from the second chamber 13 and adjacent the end of sidewall 14 (marked as entrance 25 in the figures) has a relatively large diameter, and is preferably at least 5 mm across (though it can have any convenient cross section shape). This is to prevent liquid bridging across this area, for example, under the effect of surface tension. It is also preferred that at the entrance of the passages between sleeve 8 and gas duct 6 to secondary reservoir 1 (marked as entrance 26 on the figures) that these are relatively small diameter, and that these passages preferably have a cross-sectional area of 1.4 $mm^2$ or less.

Such a combination of dimensions has been found to improve the cut-off of atomization of product in use which occurs when the user exhales. In particular, the relatively large entrance dimension 25 and small entrance dimension 26 facilitate the urging of medicament out of second reservoir 1 and back down the passages, and hence prevent unwanted atomization.

FIG. 3 shows an expanded and simplified view of secondary reservoir 1 showing entrances 25 and 26 in more detail.

In use, the atomizer according to the invention is connected to a compressed air source, which introduces a positive pressure through gas duct 6 into the atomizer, and through gas exit 4. This causes medicament in the vicinity of outlet 5 to be atomized in a known manner. When the user inhales (as shown in FIG. 1), air is drawn generally out of the atomizer via the mouthpiece 11, generating a reduced pressure in the device. In particular, first one way valve 10 is caused to open, and air is drawn in from the atmosphere. As it is drawn in, it generally captures atomized medicament, which is carried in the air stream towards mouthpiece 11 and out of the apparatus.

However, when the user has finished inhaling and subsequently exhales, this causes a positive pressure to be introduced into the atomizer, as is represented in FIG. 2. In particular, first one way valve 10 is sealed closed, but second one way valve 12 is caused to open. This in turn generates a positive pressure in second chamber 13, and this positive pressure causes expulsion of medicament from secondary reservoir 1, driving medicament back from outlet one down the channels in sleeve 8.

The effect of this is that as no medicament is to be found at this stage in the secondary reservoir 1 or outlet 5, no medicament is atomized during the exhaling part of the dosage cycle. This results in a saving in terms of the medicament used, since it is not atomized in the exhalation part of the cycle, and hence is not lost anywhere.

Any resultant extra positive pressure in the atomizer may be dissipated through resilient filter 16, which is air permeable.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. An atomizer comprising:

an atomizer jet having a product outlet from which a powdered or liquid product can be atomized;

means for sourcing compressed air;

a duct for leading the said sourced compressed air to the atomizer jet;

a product reservoir;

means for supplying the product from the reservoir to the product outlet for atomization;

a first chamber into which atomized product can diffuse; and means to prevent or stop the product from being atomized, the means to prevent or stop atomization being located between the reservoir and the product outlet and configured to stop the passage of the product to the product outlet in response to a positive pressure in the atomizer.

2. An atomizer according to claim 1, wherein the means to prevent or stop atomization includes:

a second chamber having an exit;

a secondary reservoir through which the product passes before reaching the product outlet and which is in fluid connection with the exit of the second chamber, the second chamber being operable in response to a positive pressure in the atomizer to drive fluid from the secondary reservoir.

3. An atomizer according to claim 2, wherein the second chamber includes an opening, and in that the atomizer further comprises a one-way valve which closes the opening in the second chamber.

4. An atomizer according to claim 3, wherein the one-way valve is movable between a position closing the opening in the second chamber which position permits the product to pass from the reservoir to the outlet and an open position which prevents or stops the product from passing from the reservoir to the product outlet.

5. An atomizer according to claim 3, further comprising means for controlling the position of the one-way valve.

6. An atomizer according to claim 5, wherein the means for controlling the position of the one-way valve includes an opening in the first chamber which is overlaid and closed by the one-way valve such that a positive pressure in the first chamber causes the one-way valve to open.

7. An atomizer according to claim 6, wherein the first chamber includes an air inlet, and the means for controlling the position of the one-way valve further comprises an inlet one-way valve which closes the inlet to the first chamber unless a negative pressure is present in the first chamber.

8. An atomizer according to claim 2 characterized by a rigid sidewall separating the first and second chambers.

9. An atomizer according to claim 3 wherein the one-way valve is made of a resilient material.

10. An atomizer according to claim 6 wherein the area of the opening of the first chamber closed by the one-way valve is substantially greater than the area of the opening of the second chamber closed by the one-way valve.

11. An atomizer according to claim 10 wherein the ratio of the area of the opening of the first chamber to the area of the opening of the second chamber is at least 10:1.

12. An atomizer according to claim 2 wherein the secondary reservoir includes a first entrance leading to the second chamber, and a second entrance leading into the secondary reservoir from the reservoir, and in that the first entrance is larger than the second entrance.

13. An atomizer according to claim 12, wherein the first entrance is at least 5 mm across.

14. An atomizer according to claim 12, wherein the second entrance is no larger than 1.4 $mm^2$.

15. An atomizer according to claim 1, further comprising a one-way valve which moves into an open position when the pressure within the atomizer is positive, and causes the means to prevent or stop atomization to stop the passage of the product to the product outlet.

16. An atomizer comprising:

an atomizer jet having a product outlet from which product can be atomized;

means for sourcing compressed air;

a duct for leading the said sourced compressed air to the atomizer jet;

a product reservoir;

means for supplying the product from the reservoir to the product outlet for atomization;

a first chamber into which atomized product can diffuse;

means to prevent or stop the product from being atomized, the means to prevent or stop atomization being located between the reservoir and the product outlet, and including:

a second chamber having an exit;

a secondary reservoir through which the product passes before reaching the product outlet and which is in fluid connection with the exit of the second chamber, the second chamber being operable in response to a positive pressure in the atomizer to drive fluid from the secondary reservoir; and a one-way valve which moves in to an open position when the pressure within the atomizer is positive, and causes the means to prevent or stop atomization to stop the passage of the product to the product outlet.

17. An atomizer comprising:

an atomizer jet having a product outlet from which product can be atomized;

means for sourcing compressed air;

a duct for leading the said sourced compressed air to the atomizer jet;

a product reservoir;

means for supplying the product from the reservoir to the product outlet from atomization;

a first chamber into which atomized product can diffuse; and means to prevent or stop the product from being atomized, the means to prevent or stop atomization being located between the reservoir and the product outlet, and including:

a second chamber having an exit;

a rigid sidewall separating the first and second chamber;

a secondary reservoir through which the product passes before reaching the product outlet and which is in fluid connection with the exit of the second chamber, the second chamber being operable in response to a positive pressure in the atomizer to drive fluid from the secondary reservoir, and wherein the second chamber includes an opening, and in that the atomizer further comprises a one-way valve which closes the opening in the second chamber; and wherein the secondary reservoir includes a first entrance leading to the second chamber and a second entrance leading into the secondary reservoir from the reservoir; and in that the first entrance is larger than the second entrance.

* * * * *